US006782736B1

(12) United States Patent
Hammer

(10) Patent No.: US 6,782,736 B1
(45) Date of Patent: Aug. 31, 2004

(54) METHODS AND DEVICES FOR MEASURING INTERFACE LEVELS BETWEEN FLUIDS, AND USES THEREOF

(75) Inventor: Erling Hammer, Mjolkeraen (NO)

(73) Assignee: Hammer AS, Bergen (NO)

( * ) Notice: Subject to any disclaimer, the term of this patent is extended or adjusted under 35 U.S.C. 154(b) by 0 days.

(21) Appl. No.: 10/030,827

(22) PCT Filed: Jul. 11, 2000

(86) PCT No.: PCT/NO00/00236
§ 371 (c)(1),
(2), (4) Date: Mar. 5, 2002

(87) PCT Pub. No.: WO01/07874
PCT Pub. Date: Feb. 1, 2001

(30) Foreign Application Priority Data

Jul. 12, 1999 (NO) .............................................. 993436

(51) Int. Cl.$^7$ ........................ G01N 33/20; G01N 37/00
(52) U.S. Cl. .................. 73/61.44; 73/53.01; 73/54.12; 73/304 C
(58) Field of Search ............................. 73/61.44, 53.01, 73/61.49, 54.12, 304 C, 61.45

(56) References Cited

U.S. PATENT DOCUMENTS 4,918,979 A * 4/1990 Pearce et al. .............. 73/61.41
5,251,488 A * 10/1993 Haberman et al. ....... 73/861.04
5,389,883 A * 2/1995 Harper ....................... 324/636
5,585,729 A * 12/1996 Toshima et al. ............ 324/445
5,594,163 A * 1/1997 Suzuki ...................... 73/61.44

* cited by examiner

Primary Examiner—Hezron Williams
Assistant Examiner—Rodney Frank
(74) Attorney, Agent, or Firm—Francis C. Hand; Carella Byrne et al.

(57) ABSTRACT

A method for measuring interface levels between fluids is described, characterized in that, with the aid of a magnetic field forming means, a variable magnetic field is formed in one of the fluids whereby a counterflowing magnetic field is established, being a function of the fluid properties with respect to the portion of conducting fraction in the fluid, and conductivity of the fraction; and the properties of the mentioned fluid are registered by registering the dominating impedance, alternatively resonance frequency, of the system; and by corresponding registrations of different fluid layers at the respective height levels, and in the existing interphase layers, and thereafter by mutual comparison of the mentioned properties, one or more exsisting multiphase levels are determined. A device to carry out the method is also described. For measuring concentrations/parts of a first fluid in a second fluid in multiphase mixtures, or in streams of the fluids, further methods and devices are given, including application of these.

5 Claims, 7 Drawing Sheets

FLOW CHART OF THE MEASURING SET UP IN LABORATORY.

FLOW CHART OF THE MEASURING SET UP IN LABORATORY.

BLOCK DIAGRAM OF DETECTOR ELECTRONICS

COIL IMPEDANCE AS A FUNCTION OF LEVEL IN SEPARTOR TANK
(N=10, f=11 MHz)

FLOW CHART OF EQUIPMENT FOR LEVEL MEASURING.

PRINCIPLE FOR METERING
WATER CUT IN MULTIPHASE MIXTURES.

RESULTS OF MEASUREMENTS FROM
A THREE-PHASE FLOW RIG OF OIL/WATER/GAS.

METHODS AND DEVICES FOR MEASURING INTERFACE LEVELS BETWEEN FLUIDS, AND USES THEREOF

The present invention relates to a method and a device for measuring interface levels in separation tanks, and methods and devices for measuring concentrations/parts of a conductive fraction in flowing multi-phase mixtures, and especially where the fluids are immiscible.

The inventions have particular relation to the oil industry where immiscible phases of hydrocarbons (oil and gas) and water are being handled, as there may be present salts (give salinity to the water) in the water fraction, and greater or smaller amounts of solid particles, such as sand. The invention can be applied when one handles flowing mixtures of such fluids and wishes to know relative compositions; or in connection with separation facilities where for example oil and water are to be separated from each other.

During production of crude oil, water and gas are separated from the oil onboard the production platforms with the aid of separation tanks that function according to the principle of gravitation. The process water lies at the bottom of the tank. The next layer is an oil/water emulsion. Then comes crude oil alone, which higher up passes into foam which eventually passes into pure hydrocarbon gas. To optimise the separation process, it is necessary to be able to measure the levels of the different layers. There are many devices for measuring the height of the different interface levels, but they all have their limitations and only a few can measure the heights of an emulsion layer and a foam layer.

It is an aim of the invention to provide a new method and device to measure the levels of the different layers in a separation tank.

Furthermore, it is an aim of the invention to provide a new method and device for measuring concentrations/parts of a conductive fraction in flowing multi-phase mixtures, and particularly where the fluids are mutual immiscible. In one embodiment, the invention provides a method for measuring interface levels between fluids. In this method, a variable magnetic field is established in one of the fluids whereby a counter-flowing magnetic field is established as a function of the properties of the fluid with respect to the portion of the conductive fraction in the fluid and the conductivity of the fraction. Further, the properties of the conductive fluid are registered by registering the prominent impedance or resonance frequency of the system. One or more interface levels that are present are then determined by corresponding registration in different fluid layers at different height levels and in the existent interface layers followed by mutual comparison of these properties.

In another embodiment, a method is provided for measuring concentrations of water in a flow of an oil, gas and water mixture. In this method, a flow of the mixture of oil, gas and water is directed through a pipe having an excitation coil and a detector coil around the pipe in axially spaced relation to the excitation coil. Further, the coils have a different resonant frequency from each other. In accordance with the method, an alternating voltage is applied to the excitation coil at a frequency of up to 20 MHz in order to induce a variable magnetic field in the mixture. The resulting detector voltage is then registered in the detector coil as a measure of the electrical conductivity of the water in the mixture independently of the fraction of the oil and gas in the mixture. Thereafter, the resultant detector voltage is compared against a calibration value in order to determine the concentration of water in the mixture.

In another embodiment, a flow of a mixture of oil, water and gas is passed through a pipe having a pair of excitation coils and a detector coil disposed about the pipe. In this embodiment, an alternating voltage is applied to one of the excitation coils at a frequency of up to 20 MHz while an alternating voltage of a different frequency of up to 20 MHz is applied to the other excitation coil. The resultant induced voltage in the detector coil thus contains two frequencies and are registered as a measure of the electrical conductivity of the water in the mixture independently of the fractions of oil and gas in the mixture. The amplitudes and frequencies of the induced voltage are then detected and compared to a mathematical model in order to determine the concentration of water in the mixture and the conductivity of the water in the mixture.

By plotting the induced voltage (impedance) as a function of the concentration of the water in the flowing mixture, any abrupt decline in the induced voltage with increasing water concentration may be determinative as a boundary layer between a water-continuous phase containing oil droplets in water and an oil-continuous phase containing water droplets in oil.

The principles of the invention explained in the following description are illustrated in the subsequent figures, in which.

NEW MEASURING PRINCIPLE

A variable magnetic field that penetrates a medium will induce eddy flows in the medium if the medium is electrically conductive or parts of it are electrically conductive. These eddy flows create a magnetic field which is directed against the imposed field. The counter-induced field will be proportional to the fraction of the conductive components in the medium and the electrical conductivity of these components.

The magnetic field can be generated by a coil to which current is supplied from an oscillator. The electrical impedance in the coil will then be dependent on the surrounding medium. The sensitivity increases with the frequency of the magnetic field, but the frequency is limited upwards by the penetrating depth of the field into the medium.

If such a coil is placed in a separation tank, the impedance of the coil will be lowest in water and highest in gas. In foam, oil and water/oil emulsions, we will obtain values for the coil impedance in between the mentioned extreme values. In oil-, water-, and gas mixtures it is shown experimentally that the frequency between 5 MHz and 15 MHz will be an optimal compromise between increasing sensitivity and reduction in penetration depth. The frequency is determined by the diameter of the coil and number of windings. Greatest sensitivity is obtained at the resonance frequency of the coil $$f_0 = \frac{1}{2\pi\sqrt{LC}}$$

where L is the coil inductance and C is the resulting coil capacitance between the windings.

As L is inversely proportional to the counterinduced field in the medium and C is dependent on the permittivity of the medium, the resonance frequency $f_o$ can be used to determine whether the coil is in oil, foam or gas as the capacitance C (but not the inductance L) will be different for each of these layers. Both the coil impedance and resonance frequency will be dependent on the conductivity and droplet size distribution of the conductive components (process water) at the detector coil. But it is the relative change in impedance, alternatively resonance frequency, which gives the different levels in the separation tank. The variations in the water conductivity and size distribution of water droplets in oil (oil-continuous mixture) and the size distribution of oil droplets in water (water-continuous mixture) have, therefore, no influence on the level measurements.

Figure 1:
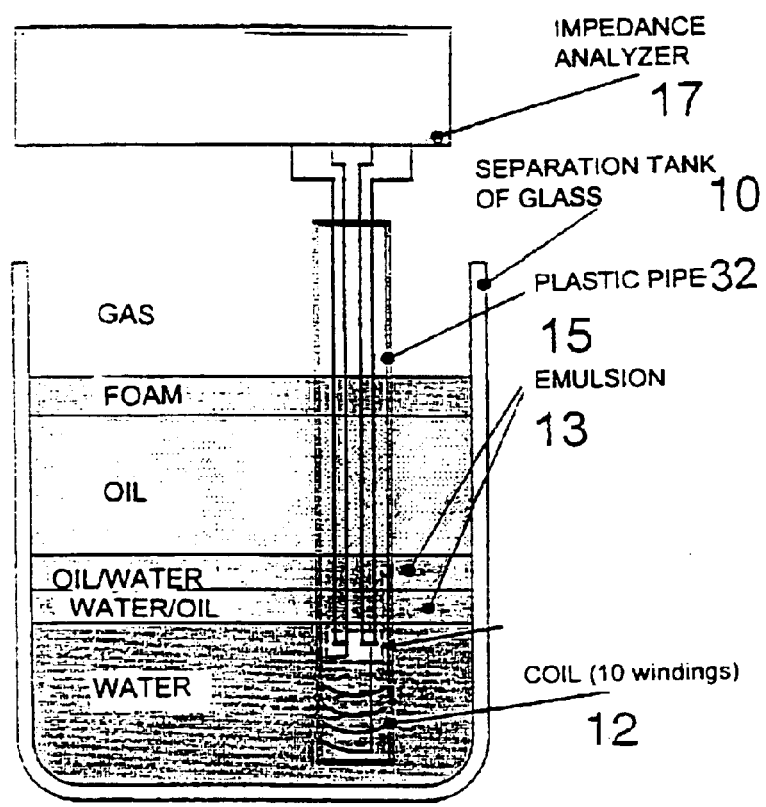
FIG. 1 shows a set-up of the device in the form of a separation tank with the phases (from below) water, oil, and gas, and intermediate boundary layers.

FIG. 1 shows a diagram of the principle of the measuring set-up in the laboratory in the form of a separation tank/container 10: typically made of glass) which contains the three phases, water, oil and gas as three separate layers in this order from below, respectively, and intermediate boundary layers. There are two emulsion layers formed between the oil phase and the water phase. The lower of these layers is a water layer 13 with a part of emulsified oil droplets which is designated a water-continuous layer, and an overlaying oil layer 15 which contains a portion of emulsified water droplets which is designated an oil-continuous layer. A measuring probe according to the invention in the form of a coil 12, and connected to an impedance analyser 17, is immersed in the container and the impedance is measured in turn in each of the above mentioned layers.

Figure 2:
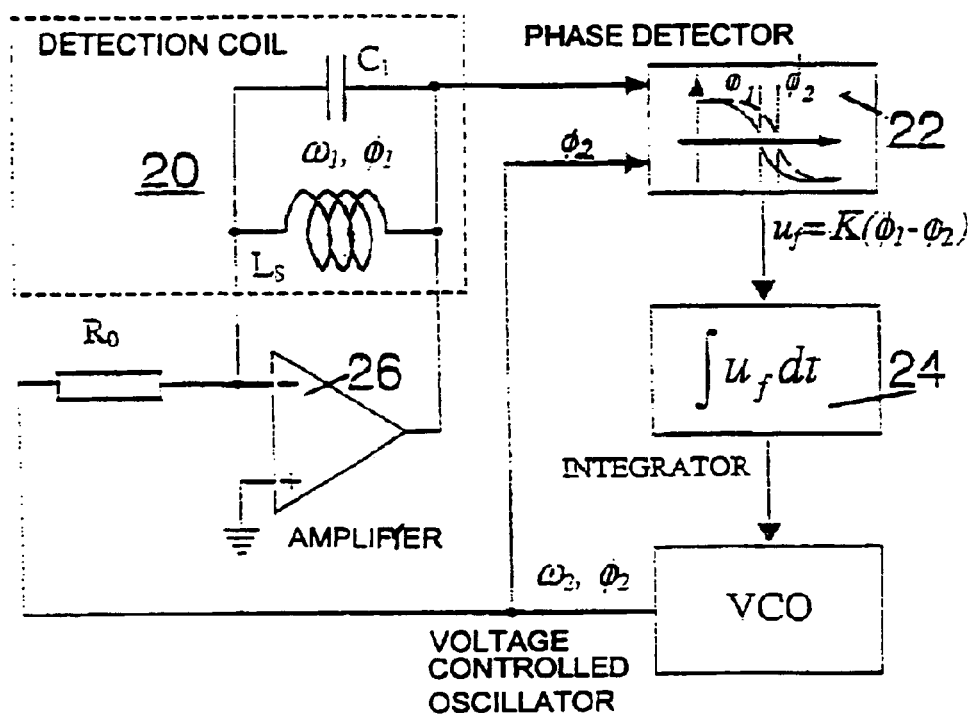
FIG. 2 shows a block diagram of the elements which are part of the detector according to the invention.

FIG. 2 shows the circuitry of the detector electronics. The circuitry consists of a detector coil 20 containing a capacitance $C_1$ connected in parallel to a coil $L_1$. An amplifier 26 is retro-connected to the coil $L_s$ and the capacitance $C_1$. Furthermore, the coil 20 is connected to a phase detector 22, which in turn is connected to an integrator 24, which in turn is connected to a voltage oscillator VCO.

The oscillator VCO is connected to the retro-connected circuit via a resistance $R_o$, and connected directly to the phase detector 22. This circuitry will ensure the excitation of the coil at resonance and make possible the measurement of the impedance of the coil and resonance frequency (at resonance the impedance is pure resistance).

Explanation of FIG. 2.

When the detector coil $L_1$ is in resonance with $C_1$, the retro-connection impedance for amplifier 26 is purely resistive and the phase displacement between $\omega_1$ and $\omega_2$ will be $-180$ degrees. In this case $\phi_1+\phi_2+0$ and the voltage from the phase detector 22 is zero. The integrator 24 will in this case have a constant terminal voltage which keeps the voltage-regulated oscillator at $\omega_2$. If the detector coil's inductivity changes by the coil being surrounded by a different material, the retro-connected network for the amplifier 26 will introduce a phase displacement such that $\phi_1+\phi_2$ is different from zero. The phase detector 22 supplies thereby a voltage which is integrated in the integrator 24 and the voltage-regulated oscillator changes the frequency $\omega_2$ until $L_1$ and $C_1$ is in resonance again and thus $\phi_1+\phi_2=0$. The frequency $\phi_2$ will thus be characteristic for the fluid with which the detector coil is surrounded.

Figure 3:
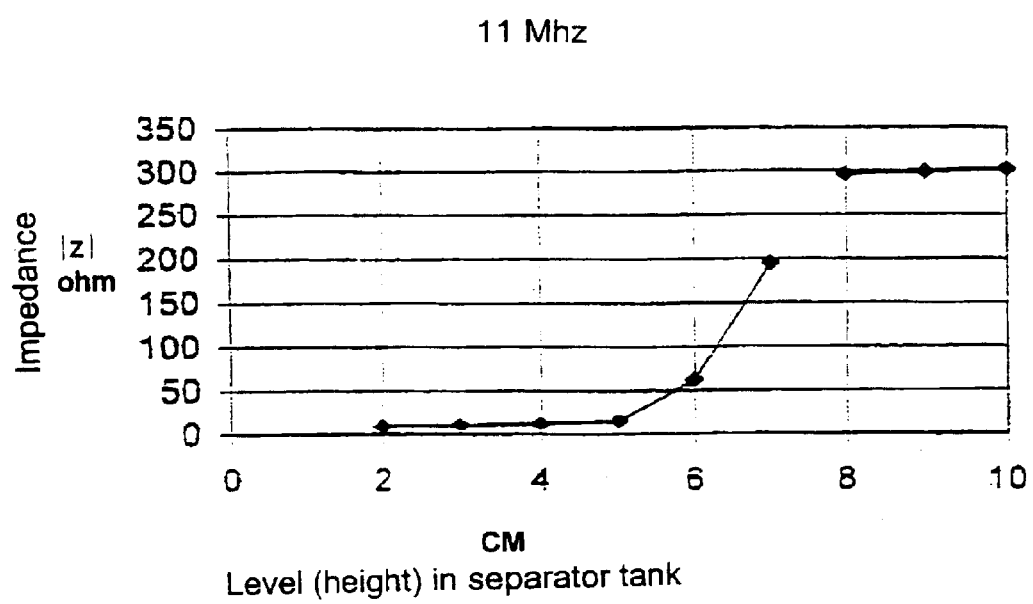
FIG. 3 shows the measuring curve for the impedance in the coil dependent on the layer in which the measuring probe is situated.

Results from the laboratory measurement with the probe connection according to the FIGS. 1 and 2 are shown in FIG. 3. The measured coil impedance is shown as a function of level in the separation tank (N=10, f=11 MHz) (N is number of windings, f is the frequency).

From the FIGS. 1 and 3 it will be clear that when the coil is surrounded by process water (e.g. water with conductivity 5 Siemens/meter), the coil impedance is low (ca. 10 ohms). It starts rising at ca. 5 cm because of water droplets in the oil. At 7 cm (in the water/oil emulsion layer) the impedance has risen to ca. 200 ohms to increase to 350 ohms in the oil phase.

Instead of using just one single coil which is manually moved consecutively to the mentioned layers, described above, one can use a submersible rod to which is mounted a number of such coils and which in total covers all the different layers, as shown in FIG. 1, as will be apparent in the next example.

The Practical Arrangement.

Figure 4:
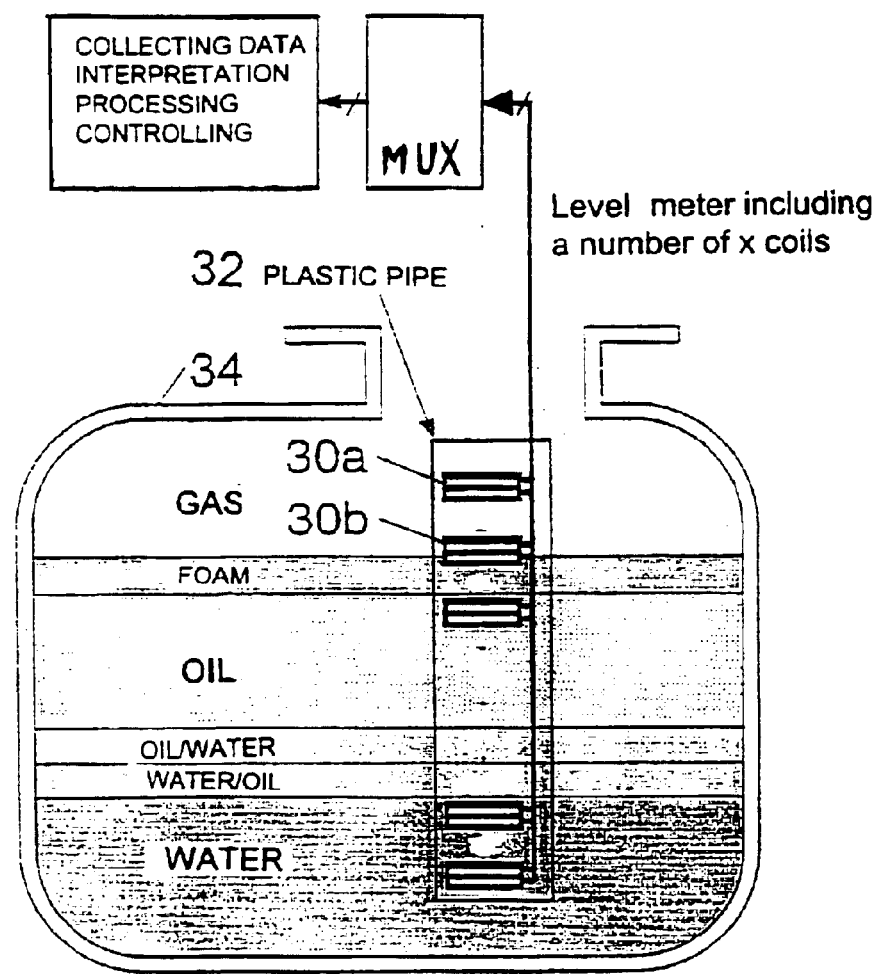
FIG. 4 shows how the invention can be used for connecting level measuring devices for measurement of levels in a container.

With reference to FIG. 4, a given number of coils 30a, 30b, . . . , 30h, (in this example 7 coils) are mounted on a submersible rod, immersed/placed in an enclosed tube 32 by electrically insulating material. The coil connections in the form of wires are led through the tube 32 to an electronics box (not shown in the figure) placed on the top of the tank 34. A standard electronics multiplexer connects the coils to the detector electronics one by one and the measuring signal from the detector electronics is sent further for interpretation, presentation, information and regulation.

The Measuring Principle Used for Measuring Water Fraction in Multiphase Mixtures.

Figure 5:
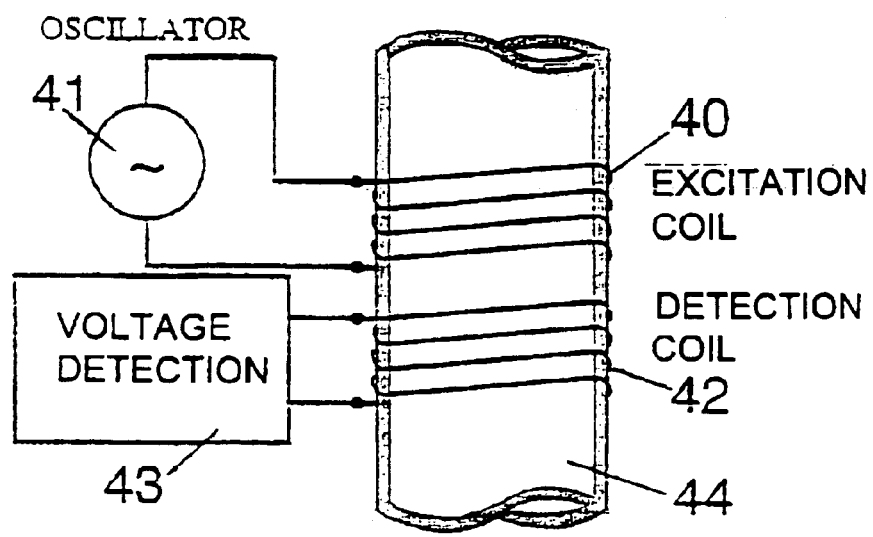
FIG. 5 shows an assembly of an excitation and a detector coil for measuring water fraction in multiphase mixtures.

This measuring principle can also be used for measuring water fraction in multiphase mixtures in which the water component is the only electrically conductive component. In this case, an excitation coil 40 with an oscillator 41 and a detector coil 42 with a voltage detector 43, as shown in FIG. 5, are used. Both coils 40, 42 are fitted to the outside of a tube of electrically insulating material 44, which carries the multiphase mixture. An oscillator establishes an alternating voltage in the coil for induction of a magnetic field through the tube. The fraction (part) of electrically conductive components in the mixture determines the strength of the induced magnetic field, and thereby the induced voltage in the detector/measuring coil.

In an oil/water/gas mixture the induced voltage in the measuring coil will be dependent on the water content, but not on the gas and oil content in the mixture, as these two components are not electrically conductive. Today in multiphase flow meters, permittivity measurement and/or gamma absorption measurement are used to determine the fractions in the mixtures. Both these measuring methods are influenced by all three components simultaneously, something which complicates the fraction estimations. The measuring principle presented here makes it possible to measure the water fraction from 0 to 100% water, independent of the amount of the other components in the mixture when these are electrically insulating. The measurements are, however, affected by the water phase conductivity, but this influence can be eliminated by using the impedance at resonance.

The droplet size distribution in the fluid mixture will also influence the measurement result, both in water-continuous and water-discontinuous phase. To compensate for this influence, a measurement with a parallel standing excitation coil with a different resonance frequency is needed. Then we have three independent measurement A variables to solve for the three unknown: Conductivity in the water component, droplet size distribution in the fluid mixture and water fraction (water cut).

The Practical Arrangement for Measuring the Water Fraction in Fluid/Gas Mixtures.

Figure 6:
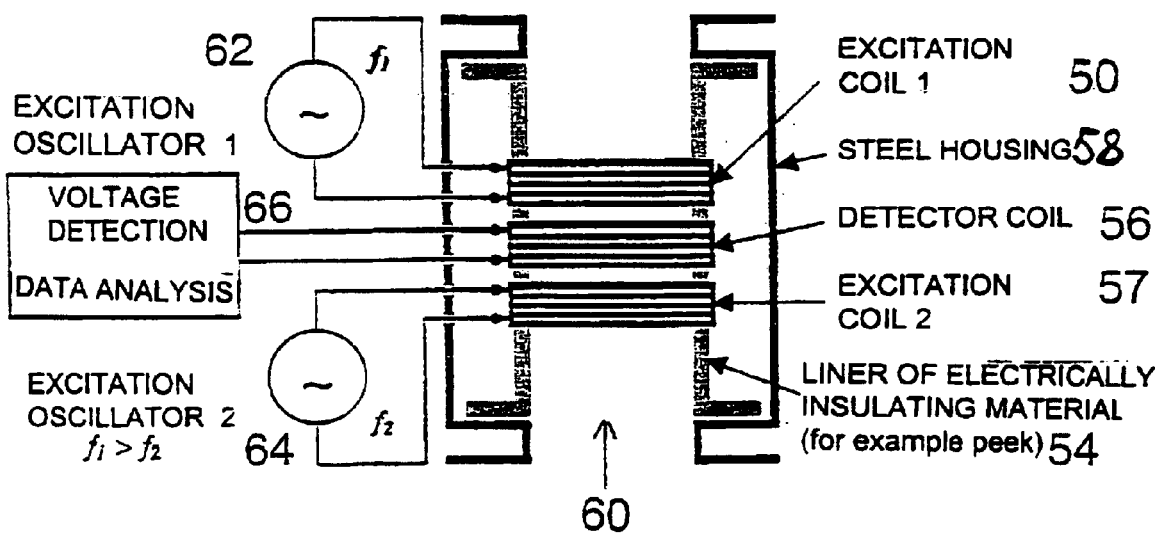
FIG. 6 shows an assembly of two excitation coils and a detector coil for measuring conductive fluid (water fraction)

The measuring unit for detection of water cut in pipe flows, is for example constructed as shown in FIG. 6.

Two excitation coils 50, 52 are wound round an insulating tube 54 (liner) made from an electrically insulating material (such as a so-called peek). Between the two excitation coils 50, 52, a detector coil 56 for the field generated by the two outer coils, is wound round the tube 54. The three coils 50, 52, 56 are mounted inside a coat 58, typically made of steel, and the whole unit surrounds the body (tube/duct) through which the fluid is flowing. The fluid flows preferably from below and upwards, as shown with the arrow 60. The two excitation coils 50,52, are connected to the excitation coils 62 and 64, respectively, which establish respective alternating voltages with different frequencies f1 and f2, for example such that f1>f2. Furthermore, the detector coil 56 is connected to a voltage detector 66 which registers the induced alternating voltage which follows from the induced counter-flowing magnetic field which arises from the water in the flowing oil. The induced voltage in the detector coil is at any time the sum of the induced voltage from the magnetic fields from the excitation coil and thus contains two frequencies. Amplitudes and frequencies are detected and water fraction and conductivity of the water are estimated with, e.g. the aid of mathematical models or a neural network.

If one frequency is used and the resonance frequency for one coil or induced voltage in the detector coil is used, the conductivity of the water must be known. The water fraction and conductivity can vary.

By using different frequencies one has two independent equations which can be used to estimate water fraction and the conductivity of the water by use of mentioned mathematical models.

Use of one frequency can provide both resonance frequency and impedance which gives two independent variables which also can be used to estimate water fraction and conductivity in the fluid.

Figure 7:
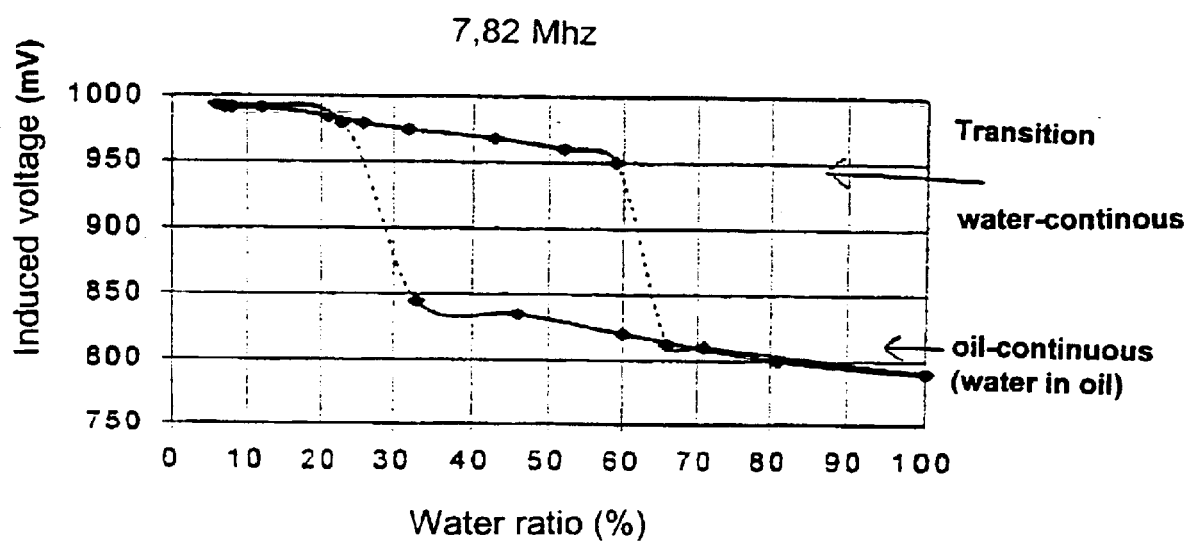
FIG. 7 shows the results from measurements carried out on a flowing mixture of oil/water/gas by application of the device shown in FIG. 6.

The experimental results from measurements carried out on a three-component flow rig (oil/water/gas) are shown in FIG. 7. The figure shows the induced voltage in millivolts as a function of the water fraction in percent. It can be seen that for both the two intermediate phases, water-continuous and oil-continuous phases, the induced voltage decreases when the water fraction increases. The tests, with the measuring points given in FIG. 7, show the abrupt decline in induced voltage with increasing water fraction at the transition between the water-continuous and the oil-continuous phases. Exactly where the fall occurs is dependent on the direction from which the measurements are taken. Either in the oil-continuous with decreasing water fraction or in the water-continuous with increasing water fraction. Thus, a hysteresis loop is obtained, and this area defines the dividing line between the two boundary layers.

The voltage-excitation/detector coils according to the FIGS. 5–6 are included in a larger circuit, such as the one which is used in connection with the FIGS. 1–4, to analyse for impedance/resonance frequency, and where comparisons are made with calibrated measurement values, such that one can provide data on the content/distribution of conductive component in the multiphase fluid. Thus one can analyse for fraction of the conductive component.

The method and device which is described in connection with the FIGS. 5–7, is particularly applicable to measuring conductive component(s) in flowing multiphase mixtures of water, oil and gas. This is relevant during exploration of hydrocarbons from an oilfield or during ordinary transport and processing of such mixtures, for example in refineries.

Such flowing mixtures are more or less mixed to emulsions, e.g. oil droplets in water (water-continuous phase) or water droplets in oil (oil-continuous phase), i.e. on a scale between pure water phase and pure oil phase. Over time, the condition in such a mixture will vary.

This means that the method and device, in combination with the use of hysteresis curve presentation as shown in FIG. 7, can be used to find out (with the aid of data processing with mathematical models or neural networks) which type of emulsion that is dominant in the flowing fluid at any time, and where on the mentioned scale the emulsion is lying (in droplets size distribution). Thus, one can all the time monitor and provide information about the condition in the multiphase flow. This is a very important application of the invention, and represents a large step forward for the oil industry.

Corresponding methodology is applied to mapping of any occurring transition-emulsions between pure oil and water phases in a tank, such as in a storage tank, as described in connection with the FIGS. 1–4. Thus, one can map where the transition between oil-continuous and water-continuous phase is lying.

In addition, the invention may be applied to all multiphase mixtures (particularly immiscible mixtures), which contain a mixture of conductive and non-conductive components. For example, generally within the chemical industry, and the food industry, such as during handling of milk, for example during homogenisation where the fraction/part of fat in the milk shall be regulated and emulsified.

What is claimed is:

1. A method for measuring concentrations of water in a flow of an oil, gas and water mixture, said method comprising the steps of directing a flow of a mixture of oil, gas and water through a pipe having an excitation coil around the pipe and a detector coil around the pipe in axially spaced relation to the excitation coil, said detector coil having a different resonant frequency from the excitation coil;

applying an alternating voltage to the excitation coil at a frequency of up to 20 MHz to induce a variable magnetic field in the mixture;

registering a resultant detector voltage in the detector coil as a measure of the electrical conductivity of the water in the mixture independently of the fractions of oil and gas in the mixture;

comparing the resultant detector voltage in the detector coil against a calibration value to determine the concentration of water in the mixture.

2. A method as set forth in claim 1 where the alternating current applied to the excitation coil is in the range of from 5 to 15 MHz.

3. An apparatus for measuring concentrations of water in a flow of an oil, gas and water mixture, said apparatus comprising a pipe for conveying a flow of a mixture of oil, gas and water;

an excitation coil around said pipe;

a detector coil around said pipe in axially spaced relation to said excitation coil, said detector coil having a different resonant frequency from said excitation coil;

an oscillator for applying an alternating voltage to said excitation coil at a frequency of up to 20 MHz to induce a variable magnetic field in the mixture;

a voltage detector for registering a resultant detector voltage in said detector coil as a measure of the electrical conductivity of the water in the mixture independently of the fractions of oil and gas in the mixture;

means for comparing the resultant detector voltage registered in said voltage detector against a calibration value to determine the concentration of water in the mixture.

4. An apparatus for measuring concentrations of water in a multiphase flow containing water, said apparatus comprising a pipe of electrically insulating material for conveying a flow of a multiphase mixture containing water as the only electrically conductive phase;

an excitation coil around said pipe;

a detector coil around said pipe in axially spaced relation to said excitation coil, said detector coil having a different resonant frequency from said excitation coil;

an oscillator for applying an alternating voltage to said excitation coil at a frequency sufficient to induce a variable magnetic field in the mixture;

a voltage detector for registering a resultant detector voltage in said detector coil as a measure of the electrical conductivity of the water in the multiphase mixture independently of the remaining phases in the multiphase mixture;

means for comparing the resultant detector voltage registered in said voltage detector against a calibration value to determine the concentration of water in the multiphase mixture.

5. An apparatus as set forth in claim 4 wherein said oscillator applys an alternating voltage to said excitation coil at a frequency of up to 20 MHz to induce a variable magnetic field in the multiphase mixture.

* * * * *